United States Patent [19]

Edgell et al.

[11] Patent Number: 4,761,367
[45] Date of Patent: Aug. 2, 1988

[54] VECTORS SUITABLE FOR DETECTION OF EUKARYOTIC DNA REGULATORY SEQUENCES

[75] Inventors: Marshall H. Edgell, Hillsborough; Steven K. Nordeen, Carrboro; Clyde A. Hutchinson, III, Chapel Hill, all of N.C.

[73] Assignee: The University of North Carolina at Chapel Hill, Chapel Hill, N.C.

[21] Appl. No.: 669,224

[22] Filed: Nov. 7, 1984

[51] Int. Cl.$^4$ .................. C12Q 1/68; C12N 15/00; C12N 5/00; C12P 21/00
[52] U.S. Cl. .......................................... 435/6; 435/68; 435/172.3; 435/320; 435/240.2; 935/9; 935/27; 935/32; 935/70; 935/71; 935/77
[58] Field of Search ................ 435/172.3, 172.6, 68, 435/253, 29, 320, 240.1; 436/501; 935/6.12–6.15, 27, 32, 36, 73, 70, 77, 79, 44, 71

[56] References Cited

U.S. PATENT DOCUMENTS

| | | | |
|---|---|---|---|
| 4,399,216 | 8/1983 | Axel et al. .................. | 435/172.3 X |
| 4,405,712 | 9/1983 | Vande Woude et al. ... | 435/172.3 X |
| 4,495,280 | 1/1985 | Bujard et al. . | |
| 4,495,287 | 1/1985 | Uhlin et al. . | |
| 4,499,189 | 2/1985 | Uhlin et al. . | |
| 4,599,308 | 7/1986 | Hamer et al. ................ | 435/172.3 X |

OTHER PUBLICATIONS

Davis, B. D. et al., Nature, vol. 283, Jan. 1980, pp. 433–438.
Roberts et al., Meth. Enzymol. 68, 473 (1979).
Cheng, S. et al., J. Bact., vol. 154, No. 2, May, 1983, pp. 1005–1008.
Dean, D., Gene, vol. 15, 1981, pp. 99–102.
Roberts, T. M. et al., Gene, vol. 12, 1980, pp. 123–127.
Gorman, C. M., et al., Mol. Cell. Biol., vol. 2, No. 9, 1982, pp. 1044–1051.
Hassell, J. A., et al., in Eukaryotic Viral Vectors, Gluzman, Y., Ed., Cold Spring Harbor Laboratory, Cold Spring Harbor, N.Y., 1982, pp. 71–77.
Rigby, P. W. J., J. Gen Virol, vol. 64, 1983, pp. 255–266.
Larsen, J. E. L., et al., Gene, vol. 28, 1984, pp. 45–54.
Linney, E., et al., Nature, vol. 308, Mar. 1984, pp. 470–472.
Okker, R. J. H., et al., Nature, vol. 312, Dec. 1984, pp. 564–566.
de Villiers, J., et al., Nature, vol. 312, Nov. 1984, pp. 242–246.
Weber, F., et al., Cell, vol. 36, Apr., 1984, pp. 983–992.

Primary Examiner—Charles F. Warren
Assistant Examiner—Jeremy M. Jay
Attorney, Agent, or Firm—Robbins & Laramie

[57] ABSTRACT

The present invention relates to vectors useful for identifying eukaryotic regulatory sequences and to a method for identifying these sequences. The vectors comprise a first nucleotide sequence which allows for replication in a eukaryotic host, a second nucleotide sequence which codes for a first product that controls replication at said first sequence, and a third nucleotide sequence which codes for a second product that is detectable. The method comprises inserting putative eukaryotic regulatory sequences at a position on the 5'-side of the second sequence and measuring the production of the second product.

20 Claims, 2 Drawing Sheets

VECTORS SUITABLE FOR DETECTION OF EUKARYOTIC DNA REGULATORY SEQUENCES

BACKGROUND OF THE INVENTION

1. Field of the Invention

The present invention relates to recombinant DNA cloning vectors which are useful for identifying eukaryotic DNA regulatory sequences. More particularly, the present invention relates to cloning vectors which contain an origin of replication that allows replication in a eukaryotic cell, a gene coding for an activator of the origin, and a DNA segment which provides a means for detecting the increased replication of the vector. A cloning site is provided upstream of the gene for cloning eukaryotic DNA sequences.

2. Description of the Prior Art

Gene expression in prokaryotes and eukaryotes can be regulated in many ways, including control of transcription, control of post-transcriptional processing, and control of translation. Gene expression can be regulated first at the developmental level, secondly at the tissue level, the thirdly at the cellular level. At the developmental level, the gene can be regulated so that it is expressed only during a specific developmental stage. The control at the tissue level occurs so that a gene will be expressed only in the proper tissue. Regulation at the cellular level occurs when the gene is being expressed at the correct developmental stage and in the correct tissue to control the amount of gene product produced. For example, the γ chain of hemoglobin is expressed in the human fetus, but is not expressed in the normal human adult. Thus there is a developmental control on the time of production of this protein. During this time of development, the expression of the gene for the γ chain is regulated so that it occurs in the erythrocyte precursor and can further be regulated by other mechanisms including those listed above.

The identification of eukaryotic regulatory sequences has many uses. The sequences which have been identified can be used in eukaryotic expression vectors. The sequences can be inserted into an appropriate site in the expression vector to regulate the expression of the desired gene. If the regulatory sequence is a strong promoter, it will drive the transcription of the desired gene to a greater extent than the natural promoter. If the regulatory sequence is an enhancer, it will enhance the transcription of the desired gene. Some regulatory sequences may be controlled by a modulator. The presence or absence of the modulator can increase or decrease the transcription of the desired gene. Thus, by appropriate control of the regulatory sequence, the gene expression can be increased. Use of regulatory sequences controlling gene expression at the tissue level is important, when the gene is inserted into tissue which may be lacking the gene (for example, as the result of a genetic disorder). Eukaryotic regulatory sequences which have been utilized for expression of genes in eukaryotic expression vectors include yeast promoters, such as alcohol dehydrogenase I, viral promoters such as the SV40 T antigen promoter, and enhancers such as those from SV40. Eukaryotic regulatory sequences identified by the present vectors can be substituted for prior art eukaryotic regulatory sequences to provide new eukaryotic expression vectors. In addition, a desired gene can be inserted into the present vectors containing a known eukaryotic regulatory sequence to produce amplification of the gene, resulting in increased expression.

Vectors have been prepared which control gene amplification as a result of increasing the replication of the vector. One such example is described in Larsen et al, *Gene* 28, 45 (1984). The vector described therein is a bacterial vector and contains a bacterial origin of replication, a bacterial gene which produces a product to activate the origin of replication, and a marker. A regulated promoter is placed upstream of the gene which can lead to increased production of the product to stimulate vector replication. These vectors have been termed conditional runaway replication vectors.

The present invention provides a vector for identifying eukaryotic regulatory sequences efficiently and quickly. The vector utilizes a gene for detection (detection gene) which can be identified quickly without the need for growing colonies. Since the vector amplifies the detection gene through increased replication, the efficiency of detection increases significantly.

SUMMARY OF THE INVENTION

The present invention comprises a vector suitable for use in eukaryotic cells and capable of receiving eukaryotic nucleotide sequences for the identification of eukaryotic regulatory sequences. The vector comprises a means for increasing vector replication as the result of the insertion of eukaryotic regulatory sequences. The vector further comprises a means for detecting the increased replication of the vector.

More specifically, the present invention comprises a vector having (a) a first nucleotide sequence which allows for replication in a eukaryotic cell.

(b) a second nucleotide sequence which codes for a first product that controls replication at said first sequence, and (c) a third nucleotide sequence which codes for a second product that is detectable.

The vector contains a cloning site on the 5'-side of the second nucleotide sequence which is suitable for inserting eukaryotic regulatory sequences. The second nucleotide sequence may optionally contain a weak promoter for low basal transcription of the first product. It is preferred that the second product be one which is positively detected, such as in an immunoassay, an enzyme assay or by staining. The vector may also contain a bacterial origin of replication and a bacterial marker gene.

A method of identifying eukaryotic regulatory sequences is described. In this method, the putative regulatory sequences are inserted on the 5'-side of the second nucleotide sequence. The sequences are regulatory if there is an increase in replication of the vector as determined by detecting the second product.

DETAILED DESCRIPTION OF THE INVENTION

Figure 1:
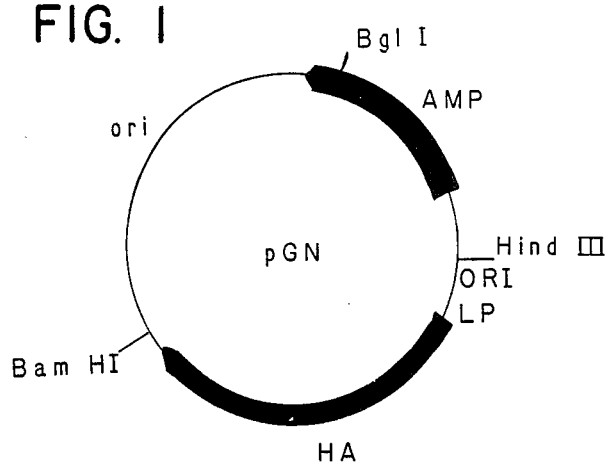
FIG. 1 is a partial restriction site and functional map of plasmid pGN.

The present invention is directed to vectors useful for identifying eukaryotic regulatory sequences, especially those sequences which regulate transcription. The present invention is also directed to a method for identifying eukaryotic regulatory sequences using the vectors of this invention. The vectors comprise a first nucleotide sequence which allows for replication of the vector in a eukaryotic host, a second nucleotide sequence which codes for a first product that controls replication at the first sequence, and a third nucleotide sequence which codes for a second product that is detectable. The vector also contains a cloning site on the 5'-side of the second nucleotide sequence. The vector may optionally contain a weak promoter as part of the second sequence to provide low basal transcription of the first product.

The vectors of the present invention are prepared by ligating together a first nucleotide sequence which allows for replication in a eukaryotic host, a second nucleotide sequence which codes for a first product which controls replication at said first sequence, and a third nucleotide sequence which codes for a second product which is detectable in a positive assay. The vectors may contain other nucleotide sequences which do not affect the functioning of the vector. Additional vectors are prepared by ligating together the above products with a fourth nucleotide sequence which contains a weak promoter. The fourth sequence is ligated to the 5'-side of the second sequence to insure low basal transcription of the vector. These vectors may also contain additional nucleotide sequences which do not affect the functioning of the vectors.

Since the vector is to be used for identifying eukaryotic regulatory sequences, it is necessary for the vector to be capable of existing in a eukaryotic host. This requires the presence in the vector of a first nucleotide sequence which allows for the replication of the vector in a eukaryotic host. Any nucleotide sequence which allows for such replication can be utilized in the vectors of the present invention. Nucleotide sequences which may be utilized for this purpose include, but are not limited to, a herpesvirus origin of replication, a papovavirus origin of replication, an adenovirus origin of replication, or a retrovirus origin of replication. Examples of specific viruses include herpes simplex virus, SV40 virus, bovine papilloma virus, human adenovirus type 5, polyoma virus, Moloney murine leukemia virus, avian sarcoma virus, Harvey murine sarcoma virus, spleen necrosis virus, and mouse mammary tumor virus.

The first nucleotide sequence may be derived from natural sources or from other recombinant DNA vectors, or it may be synthetically produced. As used herein, the term "synthetically produced" shall refer to either chemical or enzymatic synthesis. The actual sequence used is selected so that is compatible with the target eukaryotic host. An additional requirement for selecting the first nucleotide sequence is that replication at this sequence is controlled by a gene product. In the preferred embodiment, the first nucleotide sequence is the SV40 origin of replication.

The second nucleotide sequence codes for a product which controls the initiation of replication at the first sequence. The choice of the second sequence will be dictated by the first sequence which is utilized. The second sequence must regulate replication at the first sequence. This is the only restraint on the selection of the second sequence. When the second sequence is activated to produce the first product, the replication of the vector will be stimulated. This stimulation can result in the amplification of the vector by as much as 10,000- to 100,000-fold. Any nucleotide sequence which has this function can be utilized. The second nucleotide sequence may be derived from natural sources or from other recombinant DNA vectors, or it may be produced synthetically. In the preferred embodiment, the second nucleotide sequence codes for the T antigen of SV40.

The third nucleotide sequence codes for a second product which is detectable in a positive assay. As used herein, a positive assay is meant to refer to a situation in which a product is detectable directly as a result of its presence and not as the result of a growth requirement or survivability. The second product is selected so that the positive assay can be performed on a single cell. Since the product is capable of being detected in single cells, it is not necessary to identify the cells bearing the vectors as colonies, as required by other vectors. The use of this third nucleotide sequence which allows for a short assay interval also means that the DNA need not be incorporated into the chromosomes of the cell. As a result, the number of cells in the population capable of expressing the product is raised from $10^{-4}\%$ to 1-10%. As a result of using this type of detection, the vector can be detected efficiently and more quickly. The third nucleotide sequence may be derived from natural sources or from other recombinant DNA vectors, or produced synthetically. Any nucleotide sequence which produces a desired product can be utilized, except as described herein.

The third nucleotide sequence will be selected so that the product to be detected is a product normally not expressed in the eukaryotic host. Examples of suitable products include viral antigens, immunoglobulins, histocompatibility antigens, differentiation antigens, species-specific antigens, transport proteins, structural proteins, other surface proteins, enzymes and prokaryotic or cytoplasmic proteins engineered to express at the cell surface. Enzymes can be used whose activity yields a detectable product or utilizes a markable substrate. Examples of enzymes include alkaline phosphatase, P-450 type enzymes and proteases. Besides the enzyme activity detection systems which can be used, other positive detection systems include antibody-antigen systems, chromophore detection systems, enzyme-linked systems or stain systems. It is preferred to use an antibody-antigen detection system. In the preferred embodiment, the third nucleotide sequence codes for hemagglutinin antigen.

For enzyme activity detection systems it is desirable to use systems where the enzyme is extracellular or the substrate is permeable to the eukaryotic host. Alternatively, the eukaryotic host may be permeabilized to admit substrate in such a way as to maintain overall cellular structural integrity and DNA recoverability. It is not necessary that cell viability be maintained. Similarly, for the other detection systems it is desirable to use externally accessible materials, e.g., antigens, unless the eukaryotic host is permeabilized to admit the component of the detection system, e.g., antibodies. The same constraint as identified for the enzyme systems are also applicable for these detection systems in which the eukaryotic host is permeabilized.

It is further preferred that the third nucleotide sequence also contain a promoter which is constitutive for the eukaryotic host. This promoter will provide for a basal level of expression of the second product. An increase in the number of vectors will give a directly proportional increase in the amount of second product produced, thus providing for a means of detecting increased vector replication. That is, the induction signal provided by the second product will be amplified, as the vector is amplified through increased replication.

The vector may optionally contain a fourth nucleotide sequence containing a weak promoter which is placed on the 5'-side of the second nucleotide sequence. The purpose of this promoter is to provide a low basal level of transcription of the first product, thus providing for a low level of replication of the vector to insure its propagation in the eukaryotic host. Any weak promoter which will serve this purpose can be utilized. A weak promoter is desirable when the putative eukaryotic regulatory sequence does not contain a promoter but contains another type of regulatory element, such as an enhancer. By inserting putative eukaryotic regulatory sequences into both types of vectors, i.e., one with three nucleotide sequences and one with four nucleotide sequences, it will be possible to identify those regulatory sequences which contain only an enhancer rather than a promoter, or a promoter and an enhancer. The fourth sequence may be derived from natural sources or from other recombinant DNA vectors, or it may be synthetically produced. In the preferred embodiment, mouse mammary tumor virus promoter is utilized.

The vector is constructed in such a manner that a cloning site exists on the 5'-side of the second nucleotide sequence or the fourth nucleotide sequence, if it is present. This cloning site is utilized to insert the putative eukaryotic regulatory sequences. Any suitable cloning site can be utilized, and may desirably be cleavable by several different restriction endonucleases to provide a general cloning site.

Once the vector has been constructed and the putative eukaryotic regulatory sequences inserted into the cloning site, the vector is used to transform the appropriate eukaryotic host. The production of the second product by this vector is compared to the production of the second product by a vector lacking the putative eukaryotic regulatory sequences. If the sequence is a regulatory sequence with respect to gene transcription, the vector will be induced to replicate, i.e., amplified, with the resultant amplification of the detection product. If no amplification occurs, the inserted sequences are not regulatory with respect to gene transcription. If the sequence is regulatory, it can be isolated from the vector and utilized as desired, e.g., in an appropriate expression vector.

The vectors have been designed to detect and isolate any eukaryotic DNA regulatory sequence which regulates transcription. Examples of regulatory systems which might influence gene transcription via a eukaryotic DNA regulatory sequence include hormones (e.g., endocrine, exocrine or paracrine), neuroactive peptides, neuroactive transmitters, neuroactive drugs, immune system control (e.g., antigen presentation, viral or bacterial infection, interferon) mitogens, growth factors (general or tissue-specific), differentiation inducers, developmental signals, tissue-specific antigens, ions, nutrients, serum, cell extracts, stress (temperature, pH), tissue damage (wounding, biopsy), radiation (gamma-ray, X-ray, ultraviolet, infrared, visible), toxic compounds (heavy metal, alcohol, xenobiotics, metabolic inhibitors), antibiotics, lectins and plant growth factors.

The present invention will be further described by reference to the following non-limiting examples. In these examples, the preparative restriction endonuclease digestions were conducted for at least four hours unless otherwise specified. The diagnostic restriction endonuclease digestions were conducted for approximately one hour unless otherwise specified. The centrifugation in a microfuge was conducted in an Eppendorf microfuge at 12,000 to 15,000 xg unless otherwise specified. Many of the procedures, buffers and solutions utilized herein are standard, unless otherwise indicated. A suitable reference for many procedures is Maniatis, T. et al, *Molecular Cloning: A Laboratory Manual,* Cold Spring Harbor Laboratory (1982).

EXAMPLE 1

DNA Miniprep Method

The DNA miniprep method utilized herein was a modification of the procedure described by Birnboim, H. C., et al, *Nucl. Acids Res.* 7, 1513 (1979). The method is as follows. 1 ml of the overnight cultures was pelleted and the supernatant discarded. The pellet was suspended in 100 $\mu$l lysozyme solution (2 mg/ml lysozyme, 50 mM glucose, 10 mM EDTA, 25 mM Tris-HCl, pH 8.0) and left on ice for 30 minutes. At that time 200 $\mu$l of an alkaline-SDS solution (0.2N sodium hydroxide, 1% SDS) were added with gentle mixing. After five minutes at 0° C., 150 ml of 3M sodium acetate, pH 4.5, were added and mixed gently. This was incubated for about 15 minutes at $-20°$ C., then centrifuged for five minutes in a microfuge. The supernatant was transferred to a fresh Eppendorf tube and again centrifuged. The supernatant was again transferred to a fresh tube and 1 ml of ethanol was added. The tube was placed at $-70°$ C. for about 15 minutes and the DNA pelleted by centrifugation. The pellet was dried and resuspended in an aqueous solution, and the ethanol precipitation repeated twice. After drying, the pellet was resuspended in 80 $\mu$l of TE (10 mM Tris-HCl, 1 mM EDTA, pH 8.0) and an aliquot analyzed by minigel electrophoresis.

EXAMPLE 2

Restriction Endonuclease Digestions

Restriction endonucleases were obtained from Bethesda Research Laboratories, Inc. (BRL), New England BioLabs, Inc. (NEB), Boehringer-Mannheim (BM), or prepared following standard protocols (EcoRI). The endonucleases had the following units:

| Enzyme | Units/$\mu$l | Enzyme | Units/$\mu$l |
| --- | --- | --- | --- |
| BamHI | 10 | BglI | 10 |
| EcoRI | 10 | BglII | 10 |
| PvuII | 10 | SstI | 4 |
| SalI (BRL) | 4 | ClaI | 9 |
| SalI (NEB) | 10 | AvaII | 1 |
| HindIII | 10 | HindII | 10 |
| AhaII | 0.2 | | |

Digestions with EcoRI, BamHI and SalI alone or in combinations with each other were conducted in a high salt core buffer. This buffer contained 150 mM NaCl, 6 mM Tris-HCl, pH 8.0, 6 mM MgCl$_2$, 6 mM 2-mercaptoethanol and 10 μg/ml of bovine serum albumin.

Digestions with all other restriction enzymes, alone, in combination with each other, or in combination with EcoRI, BamHI and SalI were conducted in a medium salt core buffer. This buffer contained 50 mM NaCl, 6 mM Tris-HCl, pH 8.0, 6 mM MgCl$_2$, 6 mM 2-mercaptoethanol and 10 μg/ml bovine serum albumin.

EXAMPLE 3

Construction of Plasmid pGN

Plasmid pXD7, obtained from Mary-Jane Gething, Cold Spring Harbor Laboratory, was digested with HindIII and BamHI. The DNA was segregated according to molecular weight by electrophoresis through an agarose gel in "E" buffer (40 mM Tris-acetate, pH 7.2, 20 mM Na-acetate, 4 mM EDTA) overnight at 25 V. The DNA was visualized by staining the gel with 0.5 μg/ml ethidium bromide for 30 minutes. Small squares of DE81 paper were placed in the gel with forceps next to the two largest DNA fragments. The gel was then turned 90° with respect to the electric field, and the DNA was electrophoresed onto the DE81 paper at 200 V in 1/5E buffer. When the DNA had migrated to the paper, the paper was removed and placed in a 0.4 ml Eppendorf tube which had a hole punched in the bottom and had a small plug of siliconized glass wool. The paper containing the largest fragment (A) and the next largest fragment (B) were processed separately. An aliquot, 100 μl, of wash buffer (10 mM Tris pH 8.0, 1 mM EDTA, 100 mM NaCl) was added to the tube which was then placed in a larger, 1.5 ml, Eppendorf tube. This was centrifuged very briefly in a microfuge. The wash buffer collected in the larger tube was discarded. The washing step was repeated twice more. The DNA was eluted from the paper using a 50 μl aliquot of elution buffer (10 mM Tris pH 8.0, 1 mM EDTA, 1M NaCl). The paper in contact with elution buffer was allowed to stand for a few minutes and then the assembly was again centrifuged very briefly in a microfuge. This was repeated twice more so that a total elution volume of 150 μl was collected in the large Eppendorf tube. An equal volume of H$_2$O was added, followed by 1 ml of cold 95% ethanol. After allowing time for the DNA to precipitate, it was centrifuged for five minutes in a microfuge to pellet the precipitate. The pellet was washed once with cold 70% ethanol and again centrifuged. The ethanol was carefully removed, and the pellet was dried in a vacuum centrifuge. The pellet was resuspended in 40 μl of H$_2$O. One-tenth of this was removed and subjected to electrophoresis on an agarose minigel at 150 V in ½E buffer in order to monitor recovery.

6 μl of the A fragment was combined with 6 μl of the B fragment together with 1.5 μl of 10x ligase salts (0.5M Tris-HCl, 0.1M MgCl$_2$, 0.2M DTT, pH 8.0), 1.5 μl of 10x ligase additions (10 mM ATP, 500 μg/ml BSA), and 1 μl of T4 DNA ligase (2 units/μl, source: BRL). The ligation mixture was incubated for six hours at 13° C., then overnight at 4° after dilution with 45 μl of 1x ligase salts and 1x ligase additions. A control ligation was done identically except that 6 μl of H$_2$O was substituted for the B fragment in the ligation. *E. coli* strain DH1 (ATCC No. 33849) was transformed following the procedure of Hanahan (*J.Mol.Biol.* 166, 557–580 (1983)), to make competent cells. Separate transformations were performed with 18, 9, 4 or 2 μl of the ligation mix. Each transformation was plated on a single ampicillin-containing bacterial plate. Eleven transformed colonies that resulted were picked and grown overnight in L-broth. Plasmids were prepared from these cells by the rapid miniprep procedure described above. Candidate plasmids identified by this analysis were digested with BamHI plus HindIII for one hour and RNAse for five minutes. Again the digest was analyzed on agarose minigels. One clone was identified as having the appropriate configuration. This was confirmed by digesting the miniprep DNA from this clone with PvuII, EcoRI or SalI. Each digest gave the digestion pattern for the desired product which was named pGN. Plasmid pGN was subsequently transferred into a different bacterial host, *E. coli* LE392 (ATCC No. 33572), for ease in preparing large amounts of plasmid.

The transfer of pGN from *E. coli* DH1 to *E. coli* LE392 was conducted by following the colony transformation procedure of Hanahan, supra. Four colonies of LE392 on an LM plate were picked and dispersed into 200 μl of Hanahan transformation buffer. The cells were allowed to stand for 10 minutes on ice. 4 μl of pGN DNA from a miniprep of DH1 harboring pGN were added to the LE392 cells, and the incubation continued for 10 minutes on ice. The cells were plated on LM plates containing 50 μg/ml ampicillin.

A partial restriction site and functional map of the plasmid pGN is shown in FIG. 1. LP indicates the late promoter of SV40; AMP indicates the ampicillin resistance gene; HA indicates the hemagglutinin antigen gene; ORI indicates the SV40 origin of replication; and ori indicates a pBR origin of replication.

EXAMPLE 4

Construction of Plasmid pHBH

Plasmid p311 (obtained from John Majors, Washington University) was digested with the enzyme SstI. Completeness of digestion was confirmed by agarose minigel electrophoresis. The SstI cut plasmid was extracted with phenol. The aqueous layer was removed and extracted with chloroform. The aqueous layer was removed; one-tenth volume of 3M sodium acetate pH 6.0 was added, followed by 2.5 volumes ethanol. The DNA was precipitated at −20° C., then centrifuged to pellet the DNA. After drying the DNA it was resuspended in H$_2$O. The ends left by SstI digestion were made flush by combining 40 μl of the digested p311 DNA with 2.5 μl of 2 mM dNTPs, 5 μl of 10x T4 DNA polymerase buffer (0.33M Tris-acetate, pH 7.9, 0.66M potassium acetate, 0.10M magnesium acetate, 5 mM dithiothreitol, 1 mg/ml bovine serum albumin) and 3 μl (30 units) of T4 DNA polymerase. After five minutes at 37° C., EDTA was added to stop the reaction. The DNA was extracted successively with phenol, then chloroform, followed by ethanol precipitation. BglII linkers were kinased by combining 1 μl linkers (1 μg/ml), 1 μl 10x ligase additions, 1 μl 10x ligase salts, 6 μl H$_2$O and 1 μl of T4 polynucleotide kinase (10 units/μl, source: BRL) for one hour at 37° C. This was added to 10 μl of p311 in the same buffer. T4 DNA ligase, 1 μl, was added and the mixture incubated at room temperature for six hours. The ligation was stopped with EDTA, followed by phenol, then chloroform extraction. The DNA was precipitated with ethanol, the pellet washed with 70% ethanol, recentrifuged and dried. The DNA was resuspended and digested extensively with the restriction enzyme BglII. Once more the reaction was stopped with EDTA followed by extractions with phenol and chloroform. The aqueous phase was applied to a 2 ml column of Biogel A-50 in a Pasteur pipet. The buffer used was 10 mM Tris-HCl, 1 mM EDTA. 0.3M NaCl. Aliquots of the collected fractions were subjected to agarose minigel electrophoresis to monitor recovery and were precipitated with ethanol. The fractions containing DNA were suspended in H$_2$O and a portion ligated in a total volume of 100 μl with 3 μl of ligase. The ligation mix was transformed into E. coli LE392 as described previously. Plasmid minipreps were done on twelve of the resulting colonies and the DNA digested with BglII. Several DNAs that digested with BglII were identified. One plasmid was named pHBH because of the introduction of a BglII site between the HaeIII and HpaII sites of the mMTV-derived DNA sequences (mMTV refers to mouse mammary tumor virus). The identity of the plasmid was confirmed by a further digest with SstI.

Figure 3:
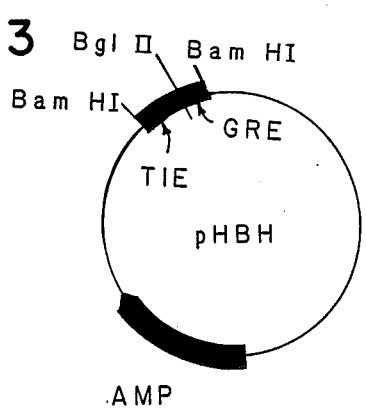
FIG. 3 is a partial restriction site and functional map of plasmid pHBH.

A partial restriction site and functional map of the plasmid pHBH is shown in FIG. 3. TIE indicates the transcription initiation element (promoter) of mMTV and GRE indicates the glucocorticoid responsive element (enhancer) of mMTV.

EXAMPLE 5

Construction of Plasmid pRN

Plasmid pK1Δ22 (obtained from Robert Gerard, Cold Spring Harbor Laboratory) was digested with BglII and BamHI, and the digest electrophoresed on a preparative agarose gel. The fragment containing the SV40 T antigen was purified with the DE81 paper technique described in Example 3.

Plasmid pSV010 (obtained from Richard Meyers, Harvard University) was digested with BglII and BamHI. The digestion was stopped with EDTA, and extracted with phenol followed by chloroform. The DNA was precipitated with 2.5 volumes ethanol, washed with 70% ethanol, dried and resuspended in 50 mM Tris, 0.1 mM EDTA, pH 8.0. One μl of calf intestinal alkaline phosphatase (25 units/μl, source: BM) was then added. This mixture was incubated for 30 minutes at 37° C. The large fragment was purified by preparative agarose gel electrophoresis and DE81 paper. The recovery of the pSV010 and pK1Δ22 fragments were quantitated by electrophoresis on minigels. Equal amounts were combined and ligated overnight. An identical control ligation was done except that H$_2$O replaced pK1Δ22 in the reaction. Transformations of E. coli LE392 were done as previously described. Transformant colonies were transferred to nitrocellulose filters, lysed, and the DNA bound to the nitrocellulose as described by Maniatis et al, supra, pg. 314, except that 2x SSC was used instead of SSPE (SSC=0.15M sodium chloride, 0.015M sodium citrate pH 7.0). The filters were exposed to a pre-wetting solution (4x SSC, 1x Denhardt's [100x Denhardt's=2% BSA, 2% Ficoll 400, 2% polyvinylpyrrolidone) for a few minutes at 42° C. The filters were then placed in the hybridization solution containing denatured. $^{32}$P-labelled T antigen DNA sequences. Per 100 ml, the hybridization solution contained 1 ml 100x Denhardt's, 85 ml formamide mix (6x SSC, 50% formamide v/v, 10% dextran sulfate w/v) and 10 ml 10x S256 (33 mM Tris pH 8.1, 8 mg % polyA, 8 mg % polyC, 0.2% yeast RNA, 3 mg % sheared E. coli DNA, 50 mg % salmon sperm DNA). The $^{32}$P-labelled probe was prepared by nick translation (J. Mol. Biol. 113-123, 1977) of the BglII - BamHI T antigen containing fragment of pK1Δ22. The nitrocellulose filters were hybridized overnight with probe at 42° C. with gentle rocking. The filters were washed twice in 2x SSC and 0.1% SDS for 15 minutes at 52° C. and five times in 0.1x SSC and 0.1% SDS for 20 minutes at 52° C. After drying the filters were placed next to autoradiography film overnight at −70° C. with an intensifying screen. Colonies aligning with positive hybridization signals were picked, and single colonies rescreened with probe. Mini plasmid preps were performed on colonies positive for both hybridization screens. A colony was identified by a DNA digest (BglII and BamHI) and agarose gel electrophoresis as having the BglII - BamHI fragment containing T antigen from pK1Δ22 cloned into BglII - BamHI cut pSV010 so as to restore both sites. This colony was selected and the plasmid named pRN.

Figure 2:
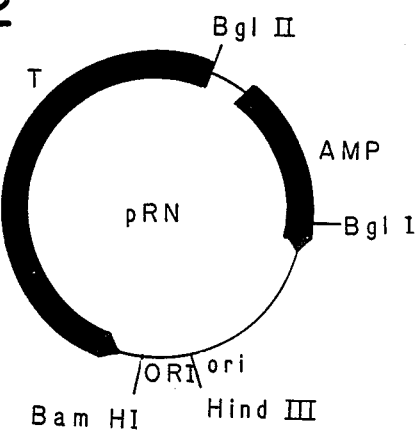
FIG. 2 is a partial restriction site and functional map of plasmid pRN.

A partial restriction site and functional map of the plasmid pRN is shown in FIG. 2. In addition to the portions described above, T indicates the SV40 T antigen.

EXAMPLE 6

Construction of Plasmid pEN-1

Plasmid pGN, prepared as in Example 3, was digested with a combination of HindIII, BamHI and AhaIII (the latter to cut down ampicillin-resistant transformants from recirculatization of the vector sequences). Plasmid pSV010 was digested with HindIII and BgII and plasmid pRN with BamHI and BgII. The reactions were stopped with EDTA and the digestions checked for completeness as follows. The digestions were extracted with an equal volume of phenol and chloroform, followed by three extractions with ether. The DNA was ethanol precipitated following evaporation of the ether. None of the DNA digests were complete, so another round of cutting/extraction/precipitation was done. A portion of the pRN digest was then phosphatased as described above, and the DNA extracted with phenol/chloroform followed by ethanol precipitation. Aliquots of the three digests were combined and ligated overnight at 14° C. at three different concentrations of DNA and enzyme. Duplication ligations were done using unphosphatased pRN digest.

The ligations were conducted in 30 μl total volumes for each method. In the first method, 1 μl of T4 DNA ligase, 1 μl of the pGN digestion (approximately 100 ng/μl), 2 μl of the pSV010 digestion (approximately 100 ng/μl) and 4 μl of the pRN digestion (approximately 25 ng/μl) were ligated as described above. In the second method, 1 μl of T4 DNA ligase, 2 μl of the pGN digestion, 4 μl of the pSV010 digestion and 8 μl of the pRN digestion were ligated as described above. In the third method, one-tenth of the amount of ligase and of the pGN, pSV010 and pRN digestions were ligated as described above.

Ligations (1 μl or 5 μl) were transformed into E. coli LE392 as described above, and transformants picked into ordered arrays on fresh plates. These colonies were grown overnight and lifted onto nitrocellulose. The filters were hybridized with $^{32}$P-labelled T antigen DNA sequences as described above. Several positive colonies were identified. Plasmid minipreps were made from these, and diagnostic restriction digests done on them using BglII and BamHI, HindIII, HindIII and BamHI, and EcoRI. A clone (from the second ligation method) was identified as having the appropriate restriction pattern to be composed of a 1.0 kb HindIII -

BglII fragment from pSV010, a 2.2 kb HindIII - BamHI fragment from pGN, and a 3.6 kb BglI - BamHI fragment from pRN. Analysis of the restriction digests previously used as well as with BamHI confirmed this structure. This plasmid was named pEN-1.

Figure 4:
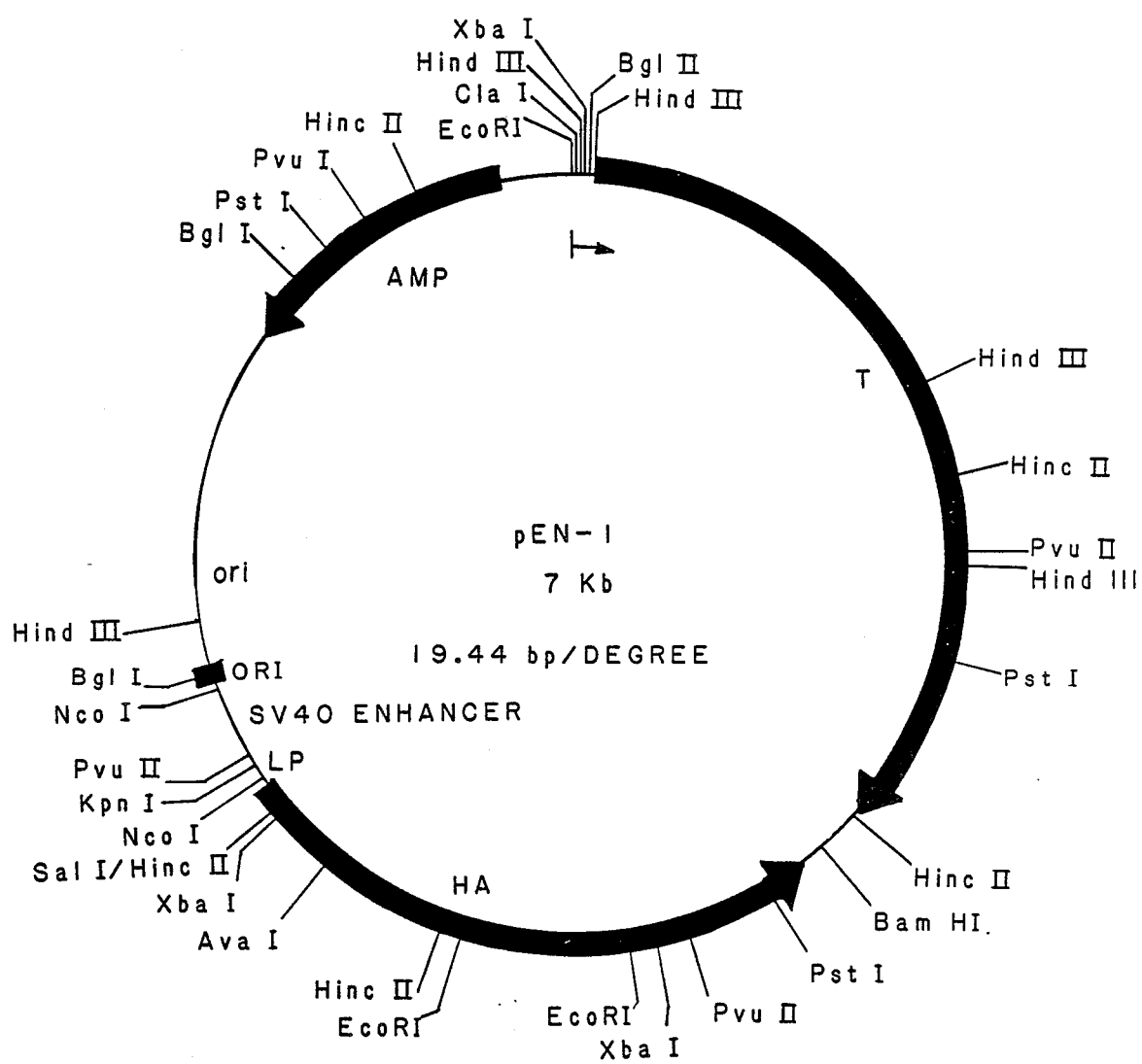
FIG. 4 is a restriction site and functional map of plasmid pEN-1.

A restriction site and functional map for the plasmid pEN-1 is shown in FIG. 4. The portions are as described above. Plasmid pEN-1 in *E. coli* LE392 was deposited at the American Type Culture Collection on Nov. 7, 1984 under the Budapest Treaty, and has been assigned No. 39915.

EXAMPLE 7

Construction of Plasmids pEN-2 and pEN-3

Plasmid pEN-1 was digested with BglII followed by phenolchloroform, then ether extractions and ethanol precipitation. The DNA was phosphatased by calf alkaline phosphatase and extracted and precipitated. Plasmid p311 was digested with BamHI and plasmid pHBH with BglII plus BamHI. The small BamHI fragment containing the mMTV promoter (TIE) and glucocorticoid response element (GRE) was isolated from p311, as was the larger of the two small BglII - BamHI fragments containing the mMTV promoter (TIE) from pHBH. Dephosphorylated, BglII cut pEN-1 was ligated to each of the two fragments above in separate reactions. The ligations were transformed into *E. coli* LE392. A number of transformants were grown overnight, and plasmid minipreps were done. Diagnostic restriction digests using ClaI and BglII, AvaII and BglII, and HindII and BglII identified a clone with a BglII - BamHI insert from pHBH into pEN-1 of the correct size and orientation. This plasmid was named pEN-2. The restriction site and functional map for pEN-2 is similar to that shown in FIG. 4 for pEN-1, except that the BglII - BamHI fragment containing TIE from pHBH (see FIG. 3) has been inserted into the BglII site 5' of the T antigen sequence. Plasmid pEN-2 in *E. coli* LE392 was deposited at the American Type Culture Collection on Nov. 7, 1984 under the Budapest Treaty, and has been assigned No. 39916.

Diagnostic restriction digests using ClaI and SstI together identified a clone with a BamHI insert from p311 into pEN-1 of the correct size and orientation. This plasmid was named pEN-3. The restriction site and functional map for pEN-3 is similar to that shown in FIG. 4 for pEN-1, except that the BamHI fragment containing TIE and GRE from p311 (see the same fragment in pHBH in FIG. 3, except that it lacks the BglII site) has been inserted into the BglII site 5' of the T antigen sequence.

EXAMPLE 8

Transformation of COS-7 Cells by pGN

Plasmid pGN was transfected into COS-7 cells as described by Mellon, P. et al, *Cell* 27, 279 (1981) or by Gluzman, Y., *Cell* 23, 175 (1981). COS-7 cells were utilized in this instance since they produce T antigen which is not produced by pGN. This insured replication of pGN. The production of hemagglutinin antigen (HA) by the infected cells was measured by a radioimmunoassay such as described by Gething, M. et al, *Nature* 293, 620 (1981). HA was produced by these cells.

EXAMPLE 9

Detection of Eukaryotic Regulatory Sequence

Plasmid pEN-2 is isolated by the miniprep procedure described above. Plasmid pEN-1 is digested with NcoI and PvuII. The smallest fragment which contains the SV40 enhancer sequences is isolated by gel electrophoresis. The ends left by NcoI cleavage are made flush by the procedure described in Example 5. ClaI linkers are then ligated to the filled-in NcoI - PvuII fragment by conventional procedures. The fragment and pEN-2 are each cleaved with ClaI, ligated together as described above, and used to transform *E. coli* LE392. A clone is identified with the appropriate restriction site map following diagnostic digestion with ClaI, and named pPE-1. This positions the SV40 enhancer element prior to the mMTV promoter and T antigen gene in pEN-2. CV-1 cells are transfected as described by Weber, F. et al, *Cell* 36, 983 (1984) with (a) pEN-2, and (b) pPE-1. The production of hemagglutinin antigen (HA) by the infected cells is measured as described above. It is found that cells containing pPE-1 produced significantly more HA than cells containing pEN-2, demonstrating an increase in replication of the recombinant vector. This indicates that pEN-2 is useful for identifying eukaryotic regulatory sequences.

EXAMPLE 10

Detection of Eukaryotic Regulatory Sequence

Plasmid pEN-1 is isolated by the miniprep procedure described above. The polyoma virus promoter is isolated by digesting the virus with BamHI and EcoRI. The smallest fragment is isolated by gel electrophoresis. The ends left by this cleavage are filled in as described above, and BglII linkers are added. The fragment and pEN-1 are each cleaved with BglII and ligated together as described above. The mixture is used to transform *E. coli* LE392. A clone is identified following diagnostic digestion with ClaI which has the proper restriction site pattern, and named pPE-2. CV-1 cells are transfected as described above with pPE-2. If the polyoma virus promoter is active, T antigen will be produced, resulting in replication of the plasmid. Plasmid pEN-1 will not replicate in CV-1 cells. The production of HA is measured as described above, and it is found that the transfected cells produce HA indicating replication of the plasmid. This indicates that pEN-1 is useful for identifying eukaryotic regulatory sequences.

While the invention has been described in connection with specific embodiments thereof, it will be understood that it is capable of further modifications. This application is intended to cover any variations, uses or adaptations of the invention following, in general, the principles of the invention and including such departures from the present disclosure as come within known and customary practice within the art to which the invention pertains.

What is claimed is:

1. A method for identifying eukaryotic regulatory sequences which comprises:
   (a) inserting putative eukaryotic regulatory sequences into a vector which comprises:
      (i) a first nucleotide sequence which provides for replication of the vector in a eukaryotic host and is the SV40 origin of replication;
      (ii) a second nucleotide sequence which codes for a first product which controls replication at said first sequence, said second sequence lacks the native promoter and the expression of which is not under the control of said promoter and said first product is SV40 large T-antigen;

(iii) a cloning site on the 5'-side of said second sequence suitable for the insertion of a putative eukaryotic regulatory sequence; and (iv) a third nucleotide sequence which codes for a second product which is different from said first product and is detectable in a positive assay, said positive assay detecting a product directly as a result of said product's presence and not indirectly as a result of a growth requirement or survivability, whereby the insertion of a eukaryotic regulatory sequence results in the amplification of the vector;

(b) transforming a first eukaroytic host with the vector of step (a);

(c) transforming a second eukaryotic host with said vector lacking the putative eukaryotic regulatory sequences; and (d) measuring the amount of said second product produced in said first and second hosts and comparing the amounts of said second product produced, whereby an increase in the amount in said first host indicates that said sequence is a regulatory sequence.

2. The method of claim 1 wherein said second product is selected from the group consisting of an antigen, an immunoglobulin, an enzyme, a transport protein, a structural protein and a protein expressed at the cell surface.

3. The method of claim 2 wherein said second product is hemagglutinin antigen.

4. The method of claim 1 wherein said vector further comprises a fourth nucleotide sequence containing a weak promoter to insure low basal transcription of said first product inserted on the 5'-side of said second sequence.

5. The method of claim 4 wherein said second product is hemagglutinin antigen and said weak promoter is the mouse mammary tumor virus promoter.

6. A vector suitable for detecting eukaryotic regulatory sequences which comprises:

(a) a first nucleotide sequence which provides for replication of the vector in a eukaryotic host and is the SV40 origin of replication;

(b) a second nucleotide sequence which codes for a first product which controls replication at said first sequence, said second sequence lacks the native promoter and the expression of which is not under the control of said promoter and said first product is SV40 large T-antigen;

(c) a cloning site on the 5'-side of said second sequence suitable for the insertion of a putative eukaryotic regulatory sequence; and (d) a third nucleotide sequence which codes for a second product which is different from said first product and is detectable in a positive assay, said positive assay detecting a product directly as a result of said product's presence and not indirectly as a result of a growth requirement or survivability, whereby the insertion of a eukaryotic regulatory sequence results in the amplification of the vector.

7. A eukaryotic host cell transformed by the vector of claim 6.

8. The vector of claim 6 wherein said second product is selected from the group consisting of an antigen, an immunoglobulin, an enzyme, a transport protein, a structural protein and a protein expressed at the cell surface.

9. The vector of claim 6 which further comprises a fourth nucleotide sequence containing a weak promoter to insure low basal transcription of said first product inserted on the 5'-side of said second sequence.

10. A eukaryotic host cell transformed by the vector of claim 9.

11. A eukaryotic vector suitable for detecting eukaryotic regulatory sequences which comprises:

(a) a first nucleotide sequence which provides for replication of the vector in a eukaryotic host and is the SV40 origin of replication;

(b) a second nucleotide sequence which codes for a first product which controls replication at said first sequence, said second sequence lacks the native promoter and the expression of which is not under the control of said promoter and said first product is SV40 large T-antigen;

(c) a cloning site on the 5'-side of said second sequence suitable for the insertion of a putative eukaryotic regulatory sequence, and (d) a third nucleotide sequence which codes for a second product which is different from said first product and is detectable in a positive assay, said positive assay detecting a product directly as a result of said product's presence and not indirectly as a result of a growth requirement or survivability, whereby the insertion of a eukaryotic regulatory sequence results in the amplification of the vector, said second product selected from the group consisting of an antigen, an immunoglobulin, an enzyme, a transport protein, a structural protein and a protein expressed at the cell surface.

12. A eukaryotic host cell transformed by the vector of claim 11.

13. The vector of claim 10 wherein said second product is hemagglutinin antigen.

14. The vector of claim 13 identified as pEN-1.

15. A eukaryotic host cell transformed by the vector of claim 13.

16. The vector of claim 11 which further comprises a fourth nucleotide sequence containing a weak promoter to insure low basal transcription of said first product inserted on the 5'-side of said second sequence.

17. The vector of claim 11 wherein said second product is hemagglutinin antigen and said weak promoter is the mouse mammary tumor virus promoter.

18. A eukaryotic host cell transformed by the vector of claim 16.

19. The vector of claim 17 identified as pEN-2.

20. A eukaryotic host cell transformed by the vector of claim 17.

* * * * *